US010564092B2

(12) United States Patent
Virot et al.

(10) Patent No.: US 10,564,092 B2
(45) Date of Patent: Feb. 18, 2020

(54) OPTICAL AND ELECTROMECHANICAL RESONATOR

(71) Applicant: Commissariat a l'energie atomique et aux energies alternatives, Paris (FR)

(72) Inventors: Leopold Virot, Voiron (FR); Vincent Agache, Chereng (FR); Jean-Marc Fedeli, Saint-Egreve (FR); Sebastien Hentz, Seyssinet Pariset (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 0 days.

(21) Appl. No.: 16/145,806

(22) Filed: Sep. 28, 2018

(65) Prior Publication Data

US 2019/0101488 A1 Apr. 4, 2019

(30) Foreign Application Priority Data

Sep. 29, 2017 (FR) ..................................... 17 59115

(51) Int. Cl.
*G01N 21/17* (2006.01)
*G01G 17/04* (2006.01)
(Continued)

(52) U.S. Cl.
CPC ......... *G01N 21/1717* (2013.01); *G01G 17/04* (2013.01); *G01N 21/255* (2013.01); *G02B 6/42* (2013.01); *H03H 9/17* (2013.01)

(58) Field of Classification Search
CPC .... G01N 21/1717; G01N 21/255; H03H 9/17; G02B 6/42; G01G 17/04
See application file for complete search history.

(56) References Cited

U.S. PATENT DOCUMENTS

2006/0233483 A1* 10/2006 Tran ................. G01N 33/54373
385/12
2010/0238454 A1 9/2010 Pruessner et al.
(Continued)

FOREIGN PATENT DOCUMENTS

WO WO 2016/069634 A1 5/2016

OTHER PUBLICATIONS

French Preliminary Search Report dated Jun. 26, 2018 in French Application 17 59115 filed on Sep. 29, 2017 (with English Translation of Categories of Cited Documents and Written Opinion).

*Primary Examiner* — Hwa Andrew Lee
(74) *Attorney, Agent, or Firm* — Oblon, McClelland, Maier & Neustadt, L.L.P.

(57) ABSTRACT

The invention is an electromechanical resonator, comprising a fixed portion and an oscillator oscillating at a resonant frequency and comprising a fluidic channel. The channel defines a fluidic circuit, can receive a fluid, and can be deformed at the resonant frequency. The resonator includes a waveguide, defining a photonic circuit, guiding a light wave between an input and an output of the waveguide and being able to be deformed at the resonant frequency. The waveguide input can be connected to a light source and the waveguide output can be connected to a photodetector able to form a signal representative of the light wave propagated by the waveguide towards the photodetector, the light wave being modulated at a frequency dependent on the resonant frequency. A variation in a mass of the fluid, inducing a variation in the resonant frequency, may be detected via the signal formed by the photodetector.

17 Claims, 10 Drawing Sheets

(51) Int. Cl.
*G01N 21/25* (2006.01)
*G02B 6/42* (2006.01)
*H03H 9/17* (2006.01)

(56) References Cited

U.S. PATENT DOCUMENTS

2013/0330232 A1 12/2013 Pruessner et al.
2015/0323466 A1 11/2015 Pruessner et al.
2017/0117905 A1 4/2017 Cermak et al.

* cited by examiner

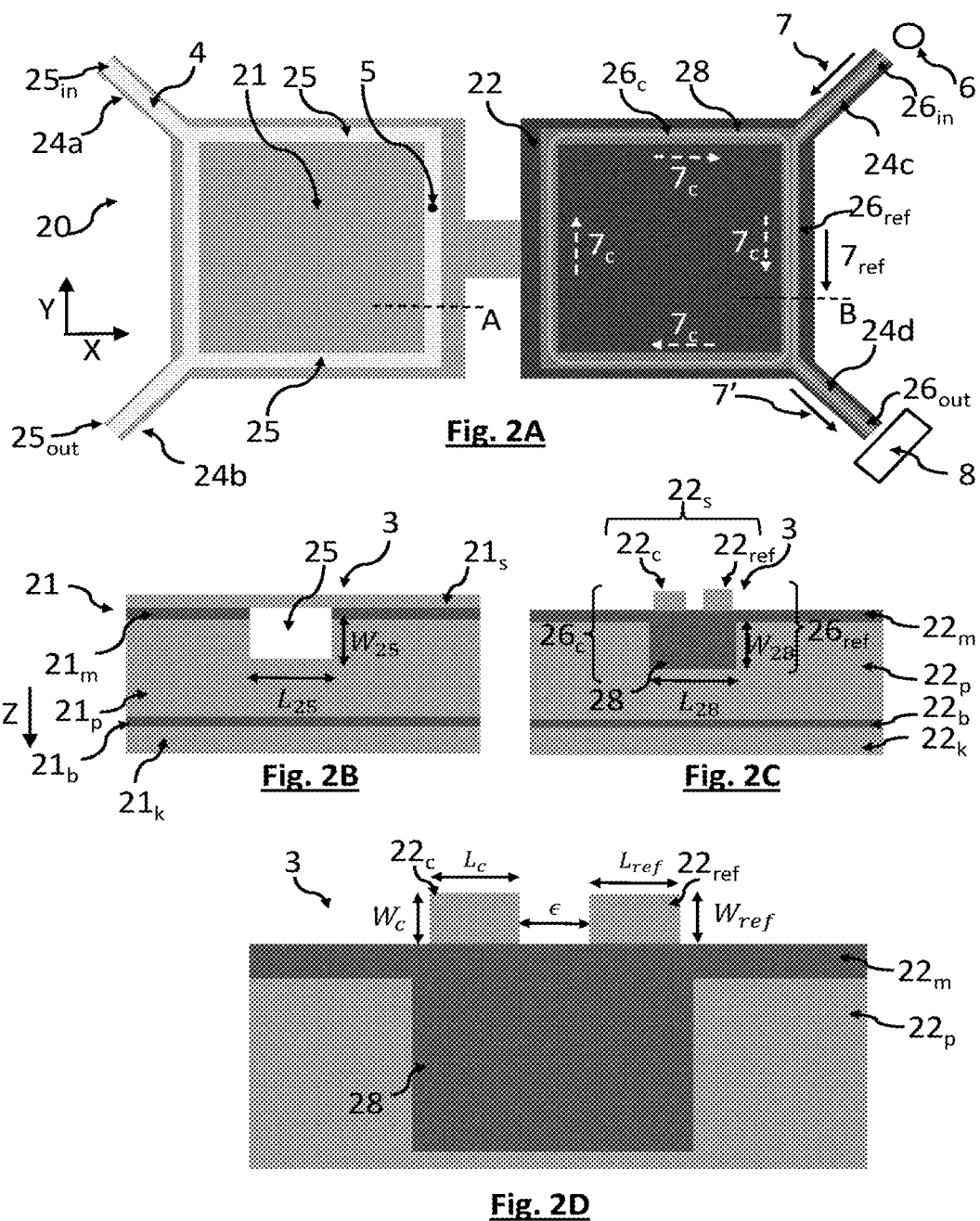

OPTICAL AND ELECTROMECHANICAL RESONATOR

TECHNICAL FIELD

The technical field of the invention is the detection of analytes with electromechanical resonators, and in particular electromechanical microresonators or electromechanical nanoresonators.

PRIOR ART

Micro-electromechanical systems (MEMS) or nano-electromechanical systems (NEMS) are commonly used in many industrial fields, as actuators or as detectors. To give a few examples, such devices are found in accelerometers, movement or pressure sensors, mobile telephones and this list is far from being exhaustive. The applications of these devices to analysis in biology or health have also been the subject of much work.

Many electromechanical devices comprise a thin movable structure that is said to be suspended above a substrate, the suspended structure being able to deform under the effect of a stress, whether it be a question of a pressure-related stress, or the application of an electric field, via a capacitive effect, or the effect of gravity or even the application of an acoustic wave. Such devices associate a mechanical aspect, in the present case a movement or a deformation of the suspended structure, and electrical means for inducing and/or detecting this movement, hence the use of the term "electromechanical". An electromechanical device may be obtained using various fabricating processes, in which various microfabrication steps are carried out one after the other, allowing a movable portion to be defined in a substrate and, on the same substrate, facing electrodes to be formed, allowing a transduction via capacitive coupling with the movable structure. Certain processes allow a piezoelectric material to be formed superposed on or adjacent to the movable structure; it is then possible to actuate or measure a movement of the movable structure via piezoelectric transduction. The movable portion may then move or deform relative to the substrate, for example so as to describe undulations or vibrations at a resonant frequency.

U.S. Pat. No. 8,844,340 describes an electromechanical resonator, the movable portion of which is passed through by a fluidic channel. The fluidic channel is functionalized, so as to retain certain particles, which are called particles of interest. During the implementation of the device, a fluid flows through the fluidic channel. When the fluid contains particles of interest, the latter may be retained in the functionalized fluidic channel. An increase in the mass of the channel results, this causing a variation in the resonant frequency. Measurement of the resonant frequency thus allows a quantity of particles present in the channel to be estimated.

U.S. Pat. No. 9,182,268 describes an electromechanical resonator comprising a fluidic circuit arranged to include sites for trapping particles depending on their size.

As described in the aforementioned patents, the movable portion of the resonator may take various forms: it may for example be a question of a cantilever or of a plate. The resonant frequency of the movable portion may be determined via various detecting means. It may be a question of a capacitive detection, by means of electrodes that are capacitively coupled to the movable portion. It may also be a question of a piezoresistive detection, the deformation of a piezoresistive material generating an electrical detection signal the frequency of which depends on the resonant frequency. It may also be a question of an optical measurement, in which a deflection of a laser beam under the effect of the vibration of the resonator is measured. Capacitive detection or piezoresistive detection require the measurement of small currents, this affecting their signal-to-noise ratio. A limited sensitivity results. Implementation of an optical measurement, such as described above, requires a precise alignment of an optical beam and optical measurement is not easily integratable into systems for industrial applications.

The inventors have designed an electromechanical resonator that makes it possible to obtain a precise estimation of resonant frequency and that is easily integratable into resonators.

SUMMARY OF THE INVENTION

A first subject of the invention is an electromechanical resonator, comprising a fixed portion and an oscillator, the oscillator being configured to oscillate at a resonant frequency, the oscillator comprising:
  a fluidic channel, defining a fluidic circuit, produced in the oscillator, and intended to receive a fluid, the fluidic channel being configured to be deformed at the resonant frequency, under the effect of the oscillation of the oscillator;
the electromechanical resonator further including:
  a waveguide, defining a photonic circuit, produced in the oscillator, and intended to guide a light wave between an input and an output of the waveguide, the waveguide being configured to be deformed at the resonant frequency, under the effect of the oscillation of the oscillator;
  the input of the waveguide being configured to be optically coupled to a light source, the output of the waveguide being configured to be optically coupled to a photodetector, so that the photodetector is able to form a signal representative of the light wave propagated by the waveguide towards the photodetector, the light wave being modulated at a modulation frequency dependent on the resonant frequency;
such that when under the effect of a variation in a mass of the fluid, inducing a variation in the resonant frequency, the variation in mass may be detected by measuring the modulation frequency or by measuring the variation in the modulation frequency of the signal formed by the photodetector.

Preferably, the fluidic channel and the waveguide extend, in the oscillator, while being, at least partially, symmetric with respect to each other. The symmetry may in particular be with respect to a point of the oscillator or with respect to an axis passing through the oscillator or extending across the oscillator.

Preferably, the oscillator oscillating at an amplitude, the oscillator comprises oscillation antinodes, level with which the amplitude of the oscillation is maximal, and oscillation nodes, level with which the amplitude of the oscillation is minimal, the fluidic channel and the waveguide extending through at least one oscillation antinode. This allows the deformation of the fluidic channel and of the waveguide under the effect of the oscillation to be maximized.

The waveguide may in particular comprise:
  a layer, in particular a thin layer, of a first material, of a first refractive index;
  a solid channel, formed from a second material, of a second refractive index, the second refractive index being strictly lower than the first refractive index, the solid channel being produced, in the oscillator, under the thin layer, such that the light wave is able to propagate in the thin layer produced facing the solid channel.

The waveguide may comprise a third material, of a third refractive index, the third refractive index being strictly lower than the first refractive index. The third material may be an ambient material, in which the resonator is located. It may also be a question of a material of an encapsulating layer, produced on the layer formed from the first material. The third material may be identical to the second material.

Thus, the layer, produced from the first material, forms a core of the waveguide, allowing a confinement of the light wave to said layer.

The fluidic channel may define a fluidic volume, and the solid channel may define a confining volume, the resonator being such that the fluidic volume, multiplied by the density of the fluid able to flow through the fluidic channel, is equal, to within 30%, to the confining volume multiplied by the density of the second material.

The resonator may comprise at least one anchoring element, joining the oscillator to the fixed portion. The fluidic circuit and/or the waveguide may extend along the anchoring element.

Preferably, the oscillator extends, in a main plane, along a width or a length or a diameter, the thickness of the oscillator, perpendicular to the main plane, being at least ten times smaller than said width, length or diameter.

According to one embodiment, the oscillator comprises a plurality of elementary oscillators, such that the fluidic circuit is produced in a first elementary oscillator and that the waveguide is produced in a second elementary oscillator, different from the first elementary oscillator, the first elementary oscillator and the second elementary oscillator being joined to each other by a linking element. The linking element preferably lies between two respective oscillation antinodes of the first elementary oscillator and of the second elementary oscillator. Preferably, the first elementary oscillator and the second elementary oscillator are able to oscillate at the same resonant frequency.

Each of the first elementary oscillator and the second elementary may extend, in a main plane, along a width or a length or a diameter, the thickness of each elementary oscillator, perpendicular to the main plane, being at least ten times smaller than the width, length or diameter.

The electromechanical resonator may comprise an actuating transducer, configured to induce an oscillation of the oscillator, the actuating transducer being:

an electrode, configured to act on the oscillator by electrostatic transduction;
or a piezoelectric element, joined to the oscillator.

Preferably, the actuating transducer lies between the fixed portion of the resonator and the oscillator. It may in particular be placed in a gap between the fixed portion and the resonator.

According to one embodiment, the waveguide may comprise a reference waveguide that is optically coupled to a resonant optical cavity, said reference waveguide and optical cavity being arranged such that the photodetector is able to detect a light wave comprising a reference light wave, which propagates through the reference waveguide, and a portion of what is called a confined light wave, which propagates through the resonant optical cavity. According to this embodiment, a portion of the light wave guided through the reference waveguide may, by optical coupling, propagate into the resonant optical cavity. A portion of the light wave guided in the resonant optical cavity may decouple from the optical cavity and propagate into the reference waveguide.

According to one embodiment, the waveguide defines a guided optical path in the oscillator, and the resonator comprises a reference waveguide, extending out of the oscillator, and defining a reference optical path. The reference waveguide is then able to be coupled to the light source and to the photodetector. The reference waveguide may define an optical path that is identical to the optical path between the light source and the photodetector, along the waveguide extending over the oscillator.

Another object of the invention is a method for analysing a fluid, containing particles, using an electromechanical resonator according to the first object of the invention, the method comprising:

a) introducing the fluid into the fluidic channel;
b) actuating the oscillator, so as to induce oscillations of the oscillator at a resonant frequency;
c) illuminating the waveguide with a light source, which emits a light wave, such that the waveguide is able to propagate the light wave emitted by the light source through the oscillator;
d) detecting, with a photodetector, a light wave transmitted by the waveguide, and modulated by the oscillation of the oscillator, and forming a signal representative of the detected light wave, the signal thus formed being modulated at a modulation frequency, the modulation frequency depending on the resonant frequency of the oscillator;
e) estimating a mass of the fluid depending on the modulation frequency, or on a variation in the modulation frequency, of the signal formed in d).

According to an embodiment, d) comprises forming a signal of interference between the light wave transmitted by the waveguide and a reference light wave emitted by the light source and transmitted by a reference waveguide. The reference waveguide may extend out of the oscillator.

According to an embodiment, the waveguide is able to confine the light wave emitted by the light source, a portion of the light wave, decoupled from the waveguide, propagating towards the photodetector, the intensity of the light wave decoupled from the waveguide being modulated at a modulation frequency dependent on the function of the resonant frequency of the oscillator.

Other advantages and features will become more clearly apparent from the following description of particular embodiments of the invention, which are given by way of nonlimiting example, and shown in the figures listed below.

FIGURES

FIG. 1A shows an example of a resonator according to the invention. FIG. 1B shows nodes and antinodes of oscillation amplitude of the resonator.

FIG. 2A shows the configuration of a fluidic channel and a waveguide in the resonator described with reference to FIG. 1A. FIGS. 2B and 2C are cross-sectional views of two portions of FIG. 2A, respectively. FIG. 2D is a detail of FIG. 2C.

Figure 4A:
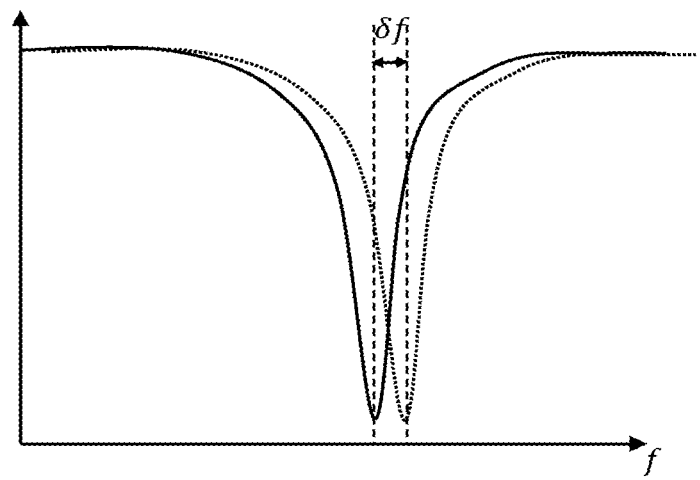
Figure 4B:
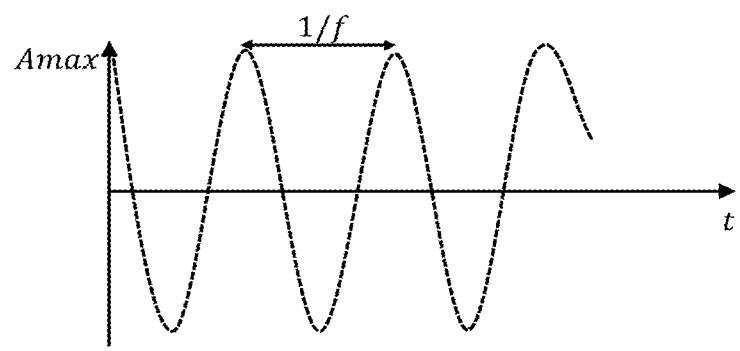
Figure 4C:
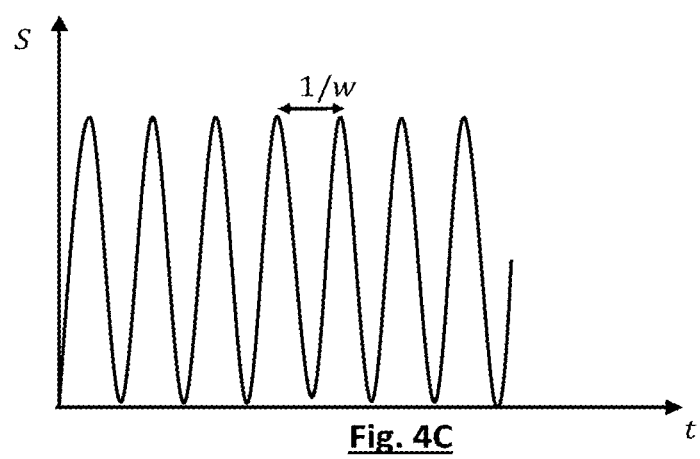

FIG. 4A illustrates a variation in a resonant frequency of a resonator. FIG. 4B schematically shows the deformation of an oscillator at a resonant frequency. FIG. 4C shows the variation in an intensity of a signal formed by a photodetector, resulting from the oscillator deformation shown in FIG. 4B.

FIGS. 5A to 5F show various arrangements of electrodes for actuating the resonator using a capacitive effect.

Figures 6A, 6B:
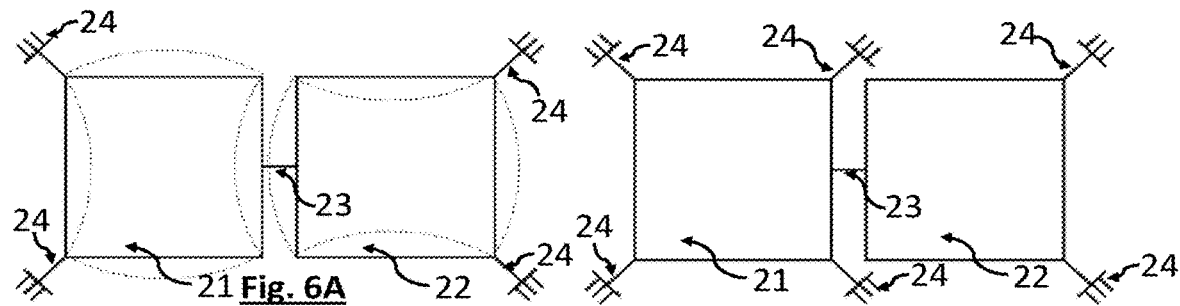
Figure 6C:
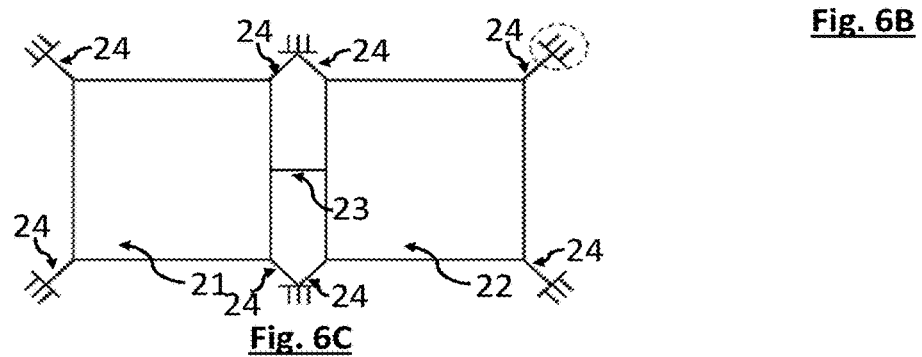

FIGS. 6A to 6C show various arrangements of anchoring elements between the oscillator of the resonator and the fixed portion of the resonator.

Figures 7A, 7B:
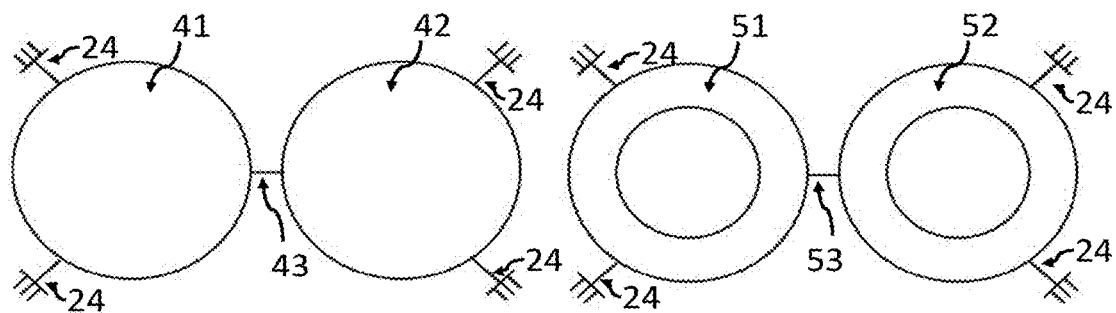
Figure 7C:
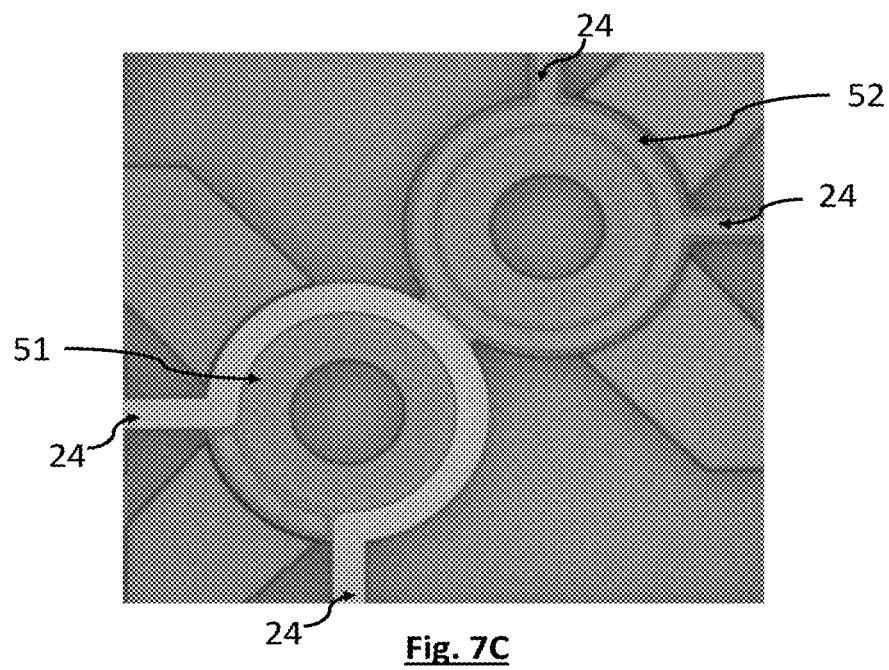

FIGS. 7A and 7B schematically show various possible resonator geometries. FIG. 7C is a photograph of a resonator such as shown in FIG. 7B.

Figure 8:
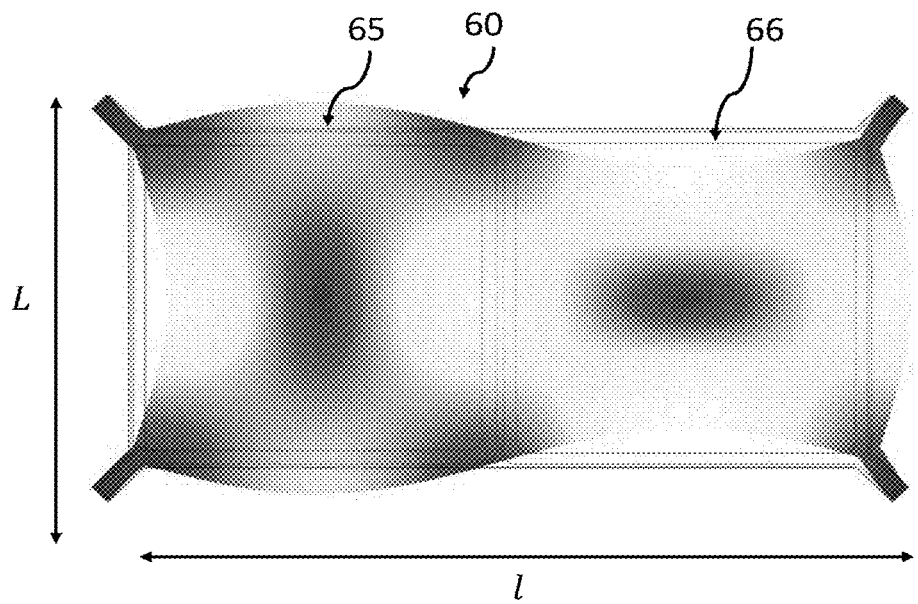

FIG. 8 shows another embodiment of the invention.

DESCRIPTION OF PARTICULAR EMBODIMENTS

Figure 1A:
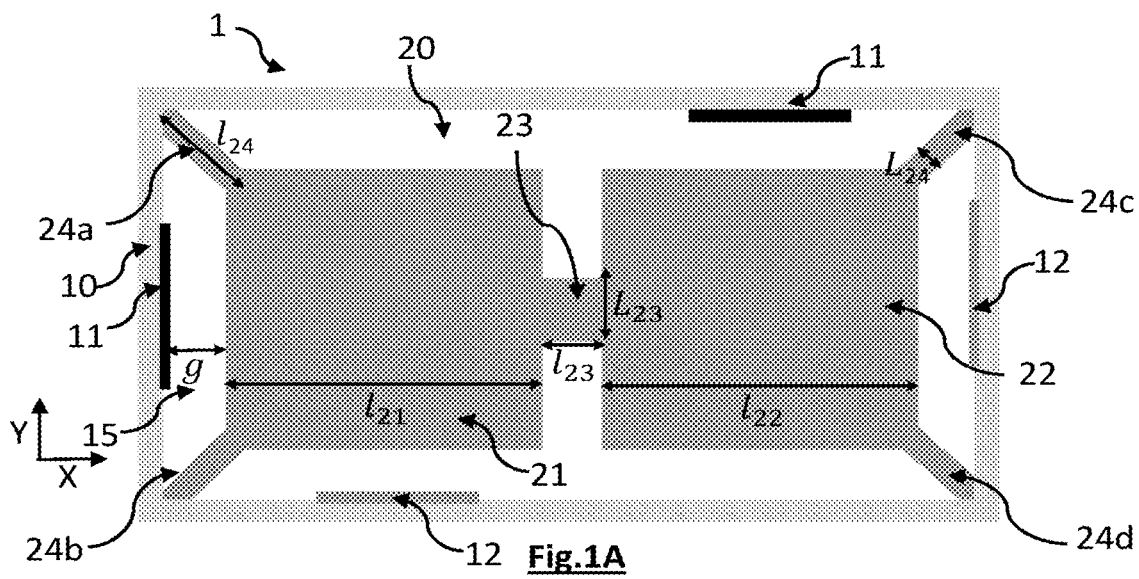

FIG. 1A shows a first example of a resonator 1 according to the invention. The resonator comprises a fixed portion 10 and a movable portion 20, forming an oscillator. The fixed portion 10 is separated from the movable portion 20 by a gap 15. The fixed portion is formed from a silicon substrate 2, the movable portion 20 and the gap 15 resulting from steps of etching the substrate. FIG. 1A shows a view of the resonator in a main XY-plane. The substrate used is a silicon substrate that will be described below with reference to FIGS. 3A to 3J. The oscillator, i.e. the movable portion 20, is, in this example, formed from two square plates 21, 22, of lengths $l_{21}$, $l_{22}$ equal to 100 µm, that are joined by a linking element 23, the latter taking the form of a beam. The thickness of the fixed portion 10, in a Z-direction perpendicular to the main plane, is for example a few hundred µm. The length $l_{23}$ of the linking element 23, along the X-axis, is about 10 µm. The width $L_{23}$ of the linking element, along the Y-axis, is 33 µm. The thickness of the movable portion 20, i.e. of the first plate 21, of the second plate 22 and of the linking element 23, in the Z-direction, is for example 5 µm. It is conventional in plate oscillators for the width (or length) to thickness ratio to be comprised between 5 and 50, and for example of the order of 20. The width g of the gap 15 between the oscillator 20 and the fixed portion 10 is of the order of a few hundred nm to a few µm, and for example 500 nm.

The movable portion 20 is connected to the fixed portion 10 by anchoring elements 24a, 24b, 24c, 24d, here taking the form of beams of length $l_{24}$ comprised between 20 and 25 µm, and of width $L_{24}$ of about 6 µm. The anchoring elements are supple. They allow the oscillator 20 to be kept joined to the fixed portion 10, while permitting an oscillation of the oscillator.

The oscillator may have other geometric configurations. It may for example be a question of a cantilever, or of a disc, or of a ring, as illustrated in FIGS. 7A to 7C, or of a single plate, as shown in FIG. 8. Whatever the embodiment, the oscillator is able to vibrate or deform at a resonant frequency f.

The fixed portion 10 comprises electrodes 11, 12 extending in the Z-direction, facing the resonator. Two electrodes have been shown placed facing the first plate 21, whereas two other electrodes are placed facing the second plate 22. The electrodes 11 are biased with a DC component $V_{DC}$ to which a first AC component $V_{AC}$ is added. The electrodes 12 are biased with the DC component $V_{DC}$, to which a second AC component $V'_{AC}$ is added, the second AC component $V'_{AC}$ being 180° out of phase with respect to the first AC component $V_{AC}$. In certain configurations, the DC component may be zero. The oscillator is then made to move using the AC components $V_{AC}$ and $V'_{AC}$ the frequency of which corresponds to half the resonant frequency of the resonator. The electrodes form a capacitive means for actuating the movable portion 20. Other actuating means are envisageable, for example piezoelectric actuation, with which the oscillator is made to vibrate using one or more piezoelectric transducers placed in contact with the oscillator.

Figure 1B:
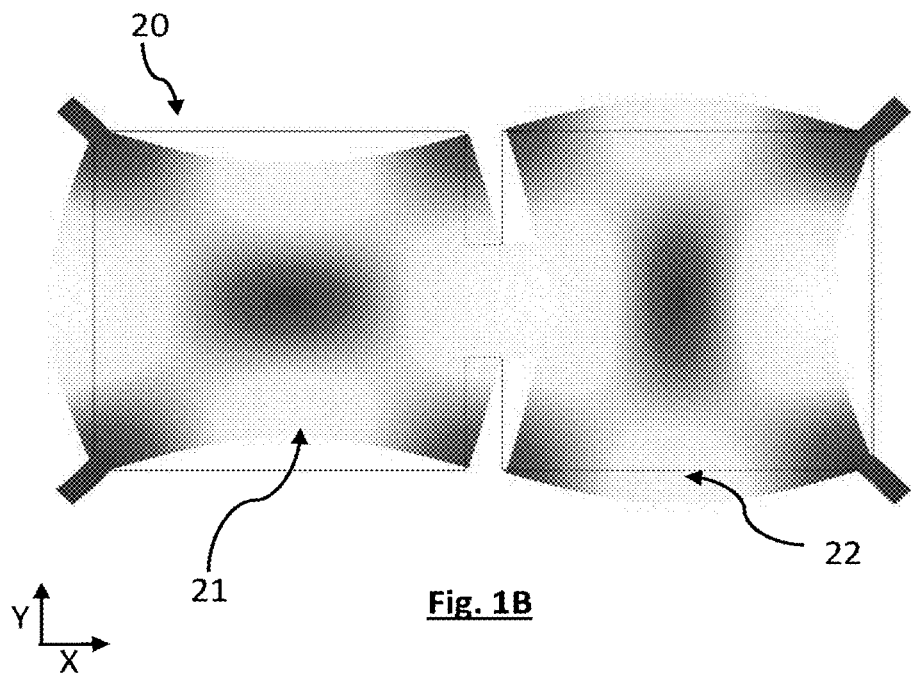

Under the effect of the electrostatic actuation, a stationary flexion wave propagates the length of each plate 21 and 22 at a resonant frequency f. FIG. 1B shows the first plate 21 and the second plate 22 in resonance in the first Lamé mode. The invention is applicable to oscillators that oscillate in other resonant modes, for example with a torsional or flexural movement. FIG. 1B was obtained by numerical simulation, using the software package COMSOL. The resonant frequency f of the first Lamé mode is given by the following expression:

$$f = \frac{1}{l\sqrt{2}}\sqrt{\frac{G}{\rho}} = 39.321 \text{ MHz}$$

where:
  l is the length of one side of a plate;
  G is the shear modulus of the material forming the plate, in the present case single-crystal silicon; and
  ρ is the density of the material forming the plate.

In this example, the dimensions of the first plate 21 and of the second plate 22 are equal, and they are made of the same material. Their resonant frequency is identical. The plates 21 and 22 are symmetric with respect to each other, about a plane of symmetry P that lies perpendicular to the main XY-plane, at equal distance from the first plate and from the second plate.

More generally, when the oscillator includes various elementary oscillators that are able to enter into resonance, the resonant frequency of each elementary oscillator is preferably substantially identical, the term substantially meaning to within a tolerance of +/−10% or +/−20%. The fact that the resonant frequency of each oscillator is identical limits the energy loss by transfer of mechanical energy between the two oscillators: the quality factor of the resonator is therefore optimal. By quality factor, what is meant is a quantity known to those skilled in the art, and representing the sharpness of a resonant peak. This resonant peak appears in a frequency spectrum, representing the amplitude of the movement of the resonator, whether it be an undulation or a vibration, as a function of frequency. The quality factor, at a resonant frequency, is determined from a width of the resonant peak appearing at said resonant frequency, for example its full width at half maximum. It may in particular correspond to a ratio between said full width at half maximum and the resonant frequency.

Alternatively, the coupling between the various elementary oscillators defines a resonant frequency of the oscillator 20, this resonant frequency being different from the respective resonant frequencies of the plate 21, forming a first elementary oscillator 21, and of the plate 22, forming a second elementary oscillator 22. Such a configuration is however less favourable from the point of view of quality factor, because of the dissipation of energy between the two elementary oscillators.

In this example, two elementary oscillators that are symmetric with respect to each other are provided: the first plate 21 and the second plate 22. It is moreover preferable for the linking element 23, joining the two plates, to be placed level with a vibration antinode of each plate, i.e. in a position corresponding to a deformation of maximum amplitude. In FIG. 1B, the vibration antinodes have been represented by light zones whereas the vibration nodes, the deformation of which is minimal, have been represented by dark zones.

Preferably, the linking element 23 does not have a resonant mode at the resonant frequency f of each plate. Moreover, the anchoring elements 24a, 24b, 24c and 24d are preferably located level with vibration nodes of each elementary oscillator.

FIG. 2A shows a top view, parallel to the main XY-plane, of an oscillator 20 comprising the two plates 21 and 22 described with reference to FIGS. 1A and 1B, forming two elementary oscillators. The first plate 21 comprises a fluidic channel 25, forming a fluidic circuit, through which a, liquid or gaseous, fluid 4 to be analyzed may flow. The fluidic channel 25 may be seen in FIG. 2A because the latter is a cutaway drawing. In this configuration, the anchoring elements 24a and 24b of the first plate 21 each comprise the fluidic channel 25, allowing the fluid 4 to enter into and output from the fluidic circuit, respectively. Preferably, the fluidic channel 25 lies parallel to the main XY-plane, in the thickness of the first plate 21. The cross section of the fluidic channel 25 may be polygonal, for example rectangular or circular. The diameter, or the longest side, of the cross section of each channel may be of the order of or smaller than half the thickness of each elementary oscillator. In this example, the cross section of the fluidic channel is square, of 4 μm side length. The fluidic channel thus extends between a fluidic inlet $25_{in}$, located in the anchoring element 24a, and a fluidic outlet $25_{out}$, located in the anchoring element 24b. The fluidic channel may comprise means for trapping a particle of interest 5 to be detected, such as chemical or hydrodynamic trapping means, as described in the prior art.

FIG. 2B schematically shows a cross section, cut along the Z-axis, of the first plate 21, the cross section being of a segment A that is shown by a dashed line in FIG. 2A. The first plate 21, the production process of which is described with reference to FIGS. 3A to 3J, consists of an upper layer $21_s$, an intermediate layer $21_m$, a main layer $21_p$, a buried layer $21_b$ and a carrier layer $21_k$. The upper layer $21_s$, the main layer $21_p$ and the carrier layer $21_k$ are made of silicon. The intermediate layer $21_m$ and the buried layer $21_b$ are made of silicon oxide. These various layers are described in the rest of the text. The fluidic channel 25 is produced in the main layer $21_p$ and in the intermediate layer $21_m$ of the first portion 21 and is closed by the upper layer $21_s$. In FIG. 2A, the layer $21_s$ covering the fluidic channel 25 has been cut away, plumb with the channel, so as to allow the fluidic channel to be seen.

FIG. 2C schematically shows a cross section of the second plate 22, cut along the Z-axis, the cross section being of a segment B that is shown by a dashed line in FIG. 2A. FIG. 2D is a detail of FIG. 2C. The second plate, the production process of which is described with reference to FIGS. 3A to 3J, consists of a structured upper layer $22_s$, an intermediate layer $22_m$, a main layer $22_p$, a buried layer $22_b$ and a carrier layer $22_k$. Just like the first portion, the upper layer $22_s$, the main layer $22_p$ and the carrier layer $22_k$ are made of silicon. The intermediate layer $22_m$ and the buried layer $22_b$ are made of silicon oxide.

The second plate 22 includes a waveguide 26, configured to form a light guide between an input $26_{in}$ and an output $26_{out}$. It also includes a channel 28, called the solid channel, of geometry similar to that of the fluidic channel 25, produced in the main layer $22_p$. The solid channel 28 is filled with a material, called the filling material, the density of which is comparable to that of the fluid 4 intended to flow through the fluidic channel 25 of the first plate 21. In the example shown in FIGS. 2A, 2C and 2D, the waveguide 26 includes a reference waveguide $26_{ref}$ that is optically coupled to a resonant photonic cavity $26_c$. As may be seen in FIG. 2C, the reference waveguide $26_{ref}$ is formed by structuring the upper layer $22_s$, so as to obtain a beam extending over the solid channel 28, forming a reference photonic channel. The resonant photonic cavity $26_c$ is formed by structuring the upper layer $22_s$, so as to obtain a ring that lies parallel to the main plane and that extends over the solid channel 28. In FIG. 2A, the direction of propagation of the light has been shown by arrows: the dashed arrows indicate the propagation of light $7_c$ confined in the resonant cavity $26_c$, whereas the solid arrows indicate the propagation of the light $7_{ref}$ in the reference guide $26_{ref}$. In FIG. 2A, the layer $22_m$ has been cut away, so as to allow the solid channel 28 to be seen.

The light 7 emitted by the light source 6 penetrates into the waveguide via a photonic input $26_{in}$, which is optically coupled to the light source 6. It exits therefrom via a photonic output $26_{out}$, the output being optically coupled to a photodetector 8. Some of the light propagating through the reference photonic channel is coupled to the resonant photonic cavity $26_c$, and its propagation confined to the latter. Some of the light $7_c$ confined to the resonant photonic cavity $26_c$ decouples from the resonant cavity in order to propagate in the reference photonic channel towards the photonic output $26_{out}$. The light wave 7', called the output light wave, that propagates towards the photodetector 8 is a combination of the reference wave $7_{ref}$ and some of the light wave $7_c$ output from the resonant cavity $26_c$.

Similarly to the fluidic channel 25, which defines a fluidic circuit, the waveguide 26 forms a photonic circuit, which lies above the solid channel 28, and which allows a light wave to propagate between the input $26_{in}$ and the output $26_{out}$. The light source may be a white light source or a light-emitting diode, preferably one coupled to an optical passband filter defining the spectral emission band about a wavelength λ that is able to propagate through the waveguide 26. It may also be a question of a laser source. The photodetector 8 may for example be a photodiode.

The waveguide 26 is formed by an etch of the upper layer $22_s$, which defines a photonic reference channel $22_{ref}$. The etch of the upper layer also allows a closed ring-shaped photonic channel $22_c$ to be formed above the solid channel 28. The closed photonic channel $22_c$ forms an optical cavity. The waveguide effect is obtained via a difference in refractive index between each photonic channel, formed by structuring the upper layer $22_s$, of refractive index $n_1$, and:
  on the one hand, the filling material of the solid channel 28, of index $n_2$, the filling material forming a second material;
  and on the other hand, the exterior medium 3 in which the resonator is located, for example air or an aqueous solution, of index $n_3$. The exterior medium thus forms a third material.

The upper layer $22_s$, after structuring, forms the core of a waveguide when $n_1>n_2$ and $n_1>n_3$. The waveguide 26 then consists:
  of the exterior medium 3 and of the filling material of the channel 28, forming confining elements of the waveguide;
  of the upper layer $22_s$, structured so as to form a reference photonic channel $22_{ref}$ or the photonic channel of the resonant cavity $22_c$, each photonic channel forming the core of a waveguide, able to propagate a light wave.

Figure 2E:
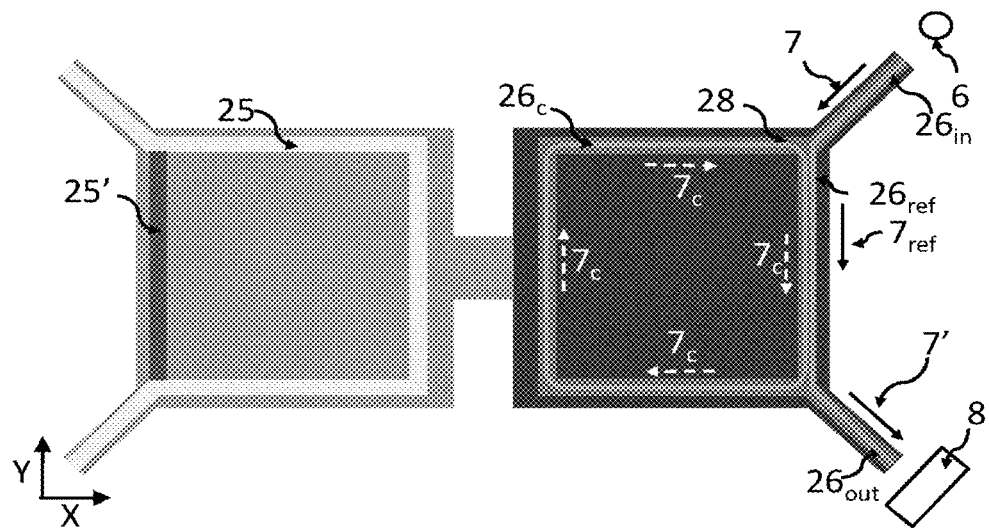
FIG. 2E illustrates a second configuration of a fluidic channel and of a waveguide in the resonator described with reference to FIG. 1A.

In the examples shown in FIGS. 2C and 2E, the photonic channels $22_c$ and $22_{ref}$ are formed by an upper layer $22_s$ of single-crystal silicon, of thickness smaller than 1 µm, the latter being, in this example, equal to 220 nm. This thickness allows a light wave of 1550 nm wavelength to propagate. The filling material with which the solid channel 28 is filled is silicon oxide. The material of such a channel may be referred to as a BOX, acronym of "buried oxide". The refractive index of the silicon oxide is about 1.45. The waveguide effect is obtained by defining photonic channels $22_c$ and $22_{ref}$ using confining elements the refractive index of which is significantly lower than the index of the upper layer, and the thickness of which is sufficient. Filling the solid channel 28 with a filling material of silicon-oxide type allows a layer that is sufficiently thick and of low refractive index to be obtained with a view to confining light in the waveguide 26, and more precisely in the reference photonic channel $22_{ref}$ and the photonic cavity $22_c$.

In this example, single-crystal silicon may be used to form the core of the waveguide 26, in particular in order to propagate a light wave in a wavelength range comprised between 1.1 µm and 1.6 µm. Propagation of a light wave through such a material requires recourse to be made to a thin layer, of submicron-sized thickness, i.e. of size smaller than or equal to 1 µm. For example, the propagation of the transverse electric mode of a light wave of wavelength λ=1550 nm through a single-crystal silicon layer requires a thin-layer thickness of 220 nm. Thus, the respective thicknesses $W_{22c}$ and $W_{22ref}$ of the photonic channels forming the resonant cavity $22_c$ and the core of the reference waveguide $22_{ref}$ are 220 nm, respectively. Their respective widths $L_{22c}$ and $L_{22ref}$ are equal to 500 nm. The spacing E between the resonant cavity $22_c$ and the reference photonic channel $22_{ref}$ is for example comprised between 200 nm and 300 nm. Generally, the term "thin layer" designates a layer with a thickness smaller than 5 µm, and preferably smaller than 1 µm or 2 µm.

Preferably, the solid channel 28 has an analogous geometry to the fluidic channel 25 located in the first plate 21, so that the respective resonant modes of the first plate 21 and of the second plate 22 are analogous. Just like the first plate 21, including a fluidic circuit, the second plate 22 includes a photonic circuit, formed by the waveguide 26, the solid channel 28 of which forms a confining element.

Figure 3A:
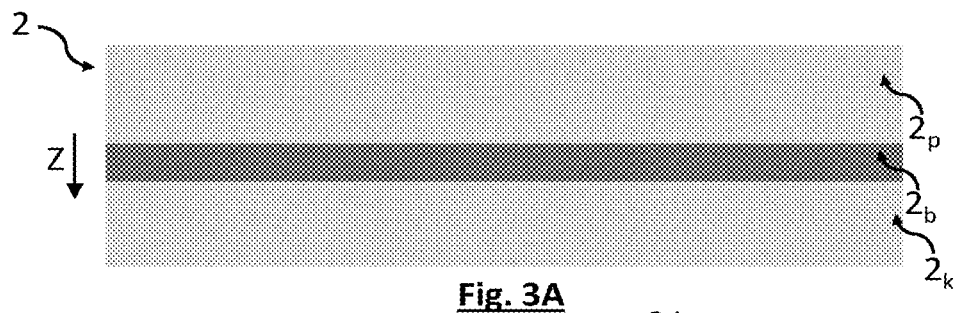
FIGS. 3A to 3J show technological steps allowing the resonators illustrated in FIGS. 2A to 2F to be produced.

It is preferable for the spatial distribution of the masses of each plate to be similar. The fluidic channel 25 extends around a first generatrix describing a first pattern in the main XY-plane. The solid channel 28 extends around a second generatrix describing a second pattern in the main XY-plane. Preferably, the first and second patterns are, partially or completely, symmetric to each other, the symmetry being understood to be with respect to a point or with respect to an axis or with respect to a plane, the plane or axis preferably being perpendicular to the main XY-plane. In the example of FIG. 3A, the patterns described by the first generatrix and the second generatrix, respectively, are symmetric with respect to the centre of the linking element 23 described above, and with respect to the plane of symmetry P described above. In order to obtain as similar as possible a distribution of the masses of each plate, this symmetry condition is combined with a condition as to the mass of the first plate 21 and of the second plate 22. In order for the respective masses of the two plates to be as similar as possible, the mass of the fluidic channel 25, filled with the fluid 4, is preferably substantially equal to the mass of the solid channel 28. This may be expressed by the following equality:

$$V_{25} \times \rho_{25} = V_{26} \times \rho_{26}, \qquad (2) \text{ where}$$

$V_{25}$ and $V_{26}$ are the respective volumes of the fluidic channel 25 and of the waveguide 26; and $\rho_{25}$ and $\rho_{26}$ are the respective densities of the fluid 4 to be analyzed and of the waveguide 26.

This amounts to writing that:

$$l_{25} \times S_{25} \times \rho_{25} = l_{26} \times S_{26} \times \rho_{26}, \qquad (3) \text{ where:}$$

$l_{25}$ and $l_{26}$ are the respective lengths of the fluidic channel 25 and of the waveguide 26; and $S_{25}$ and $S_{26}$ are the respective cross sections of the fluidic channel 25 and of the waveguide 26.

In the examples shown, the fluidic channel 25 is of square cross section, such that $S_{25} = L_{25} \times W_{25} = L_{25}^2$, $L_{25}$ and $W_{25}$ being the length and width of the fluidic channel, in the main XY-plane, respectively.

The equalities (2) and (3) may be met to within +/−10% or +/−20%, a strict equality not being necessary. In the example shown in FIGS. 2A to 2E, the structuring of the upper layer $22_s$ for forming the reference photonic channel $22_{ref}$ or the resonant cavity $22_c$ has only a marginal effect on the distribution of the mass between the two portions 21 and 22 of the resonator.

Thus, when dimensioning the fluidic channel 25, a density $\rho_{25}$ of a fluid 4 liable to be analyzed is taken into account, and the fluidic channel is dimensioned while taking into account this density.

The fluidic channel 25 has a relatively large cross section, so as to permit the fluid 4 to be analyzed to flow. Its diameter (or its largest diagonal) is larger than 1 µm, and may be as much as several µm. In the second plate 22, the geometry of the waveguide 26 is essentially defined by the geometry of the solid channel 28. The solid channel 28, filled with silicon oxide, has a thickness of $W_{28}=2$ µm, in the Z-direction, and a width $L_{28}$, in the main XY-plane, of about 4 or 5 µm. The width and thickness of the fluidic channel 25 are for example equal to 4 µm. On account of the fact that the geometry of the waveguide 26 essentially depends on the solid channel 28, the expressions (2) and (3) become:

$$V_{25} \times \rho_{25} = V_{28} \times \rho_{28} \qquad (4),$$

$$l_{25} \times S_{25} \times \rho_{25} = l_{28} \times S_{28} \times \rho_{28}. \qquad (5).$$

Since the solid channel 28 represents almost the entirety of the mass of the waveguide 26, the effect of structuring the upper layer $22_s$ to form the photonic channels $22_{ref}$ or $22_c$ may be neglected.

The pattern, defined by the solid channel 28, is, in the main XY-plane, preferably symmetric with at least one portion of the fluidic channel 25. On account of the density of silicon oxide (2200 kg/m$^3$), when the fluidic channel 25 is intended to be occupied by an aqueous solution, of 1000 kg/m$^3$ density, on account of the thickness $W_{28}$ of 2 µm of the solid channel 28, either of the expressions (2) and (3) leads to a width $L_{28}$ of the solid channel of about 3.6 µm.

When a particle 5, entrained by the fluid 4 to be analyzed, penetrates into the fluidic channel 25 and flows through the latter, the variation δm in the mass of the fluidic channel 25 induces a variation δf in the resonant frequency of the oscillator 20. By particle, what is meant is a biological particle, for example a cell, a microorganism, a spore, or a virus. It may also be a question of a mineral or organic particle, or of a gaseous particle, an air bubble for example. When the particle has the effect of increasing the weight of the fluidic channel 25, the resonant frequency decreases and δf<0. When the particle has the effect of decreasing the weight of the fluidic channel 25, the resonant frequency increases and δf>0.

An important element of the invention is that the variation δf in the resonant frequency is detected by the assembly consisting of the light source 6, the waveguide 26 and the photodetector 8. This aspect is described in more detail with reference to FIGS. 4A to 4C.

The configuration illustrated in FIG. 2A shows a case in which the fluidic channel 25 and the waveguide 26 are symmetric to each other about a median plane P that is perpendicular to the main XY-plane and that lies at equal distance from the first plate and from the second plate. Thus, the spatial distribution of the masses of the first plate 21 is identical to the spatial distribution of the masses of the second plate 22.

Other configurations are envisageable, in which the fluidic channel 25 and the waveguide 26 are only partially symmetric. By partially symmetric, what is meant is symmetric over a section of the fluidic channel 25 and of the waveguide 26. FIG. 2E for example shows a variant of the configuration shown in FIG. 2A, in which the waveguide 26 extends parallel to the four sides of the second plate 22 in a similar way to the configuration shown in FIGS. 2A, 2C and 2D. The waveguide 26 includes a reference waveguide $26_{ref}$ and a resonant cavity $26_c$. The light propagates between a photonic input $26_{in}$, which is optically coupled to a light source 6, and a photonic output $26_{out}$, which is optically coupled to a photodetector 8. Just like in the preceding configuration, the resulting light wave 7' detected by the photodetector is formed from a reference light wave $7_{ref}$, which propagates from the photonic input $26_{in}$, and a portion of the light wave $7_c$ that propagates through the resonant cavity $26_c$. The fluidic circuit 25 has a single branch, which lies parallel to three of the four sides of the first plate 21. In order to balance the respective masses of the first plate 21 and of the second plate 22, a compensating channel 25', of identical cross section to the solid channel 28, is formed in the first plate 21. The compensating channel 25' is formed from silicon oxide. Thus, the compensating channel allows the mass of the fluidic channel 25 filled with fluid and the mass of the solid channel 28 to be balanced.

Figure 2F:
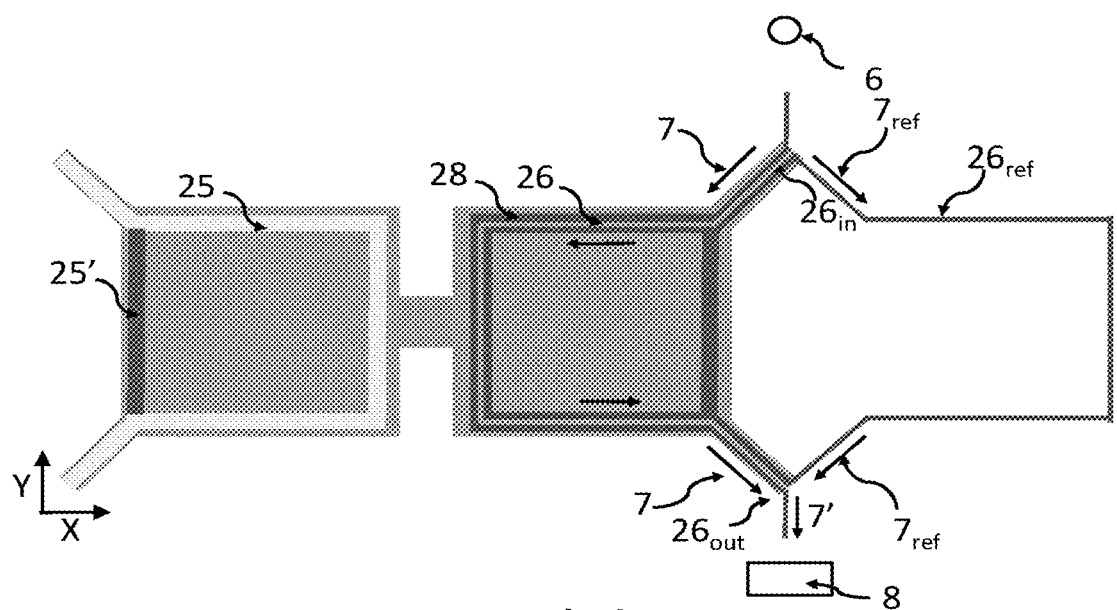
FIG. 2F illustrates a third configuration of a fluidic channel and of a waveguide in the resonator described with reference to FIG. 1A.

FIG. 2F shows a variant of the configuration shown in FIG. 2E, in which the fluidic channel 25 extends parallel to three sides of the first plate 21, whereas the waveguide extends along three sides of the second plate 22. In this configuration, the resonator includes a waveguide 26, extending over the second plate 22, and formed by structuring the upper layer $22_s$, so as to form a photonic channel of 220 nm thickness and of 500 nm width. The waveguide 26 extends between the photonic input $26_{in}$ and the photonic output $26_{out}$. In this configuration, a reference photonic circuit $26_{ref}$ is located outside of the second plate and is also coupled to the photodetector 8. Thus, the photodetector detects a resulting light wave 7' formed by a reference light wave $7_{ref}$ which propagates from the light source 6, and a light wave 7 that propagates through the waveguide 26.

Whatever the adopted configuration, it is preferable for the fluidic channel 25 and the waveguide 26 to extend through at least one deformation maximum, or antinode, of each plate, or even through each deformation maximum of each plate. The greater the deformation of the fluidic channel 25 and of the waveguide 26, the higher the sensitivity of the measurement. Simulations carried out beforehand, such as those shown in FIG. 1B, make it possible to predict the position of each deformation maximum. The definition of the path of the fluidic channel 25 and of the waveguide 26 may be based on these simulations. The notion of deformation maximum may be broadened to a zone of the oscillator in which the deformation amplitude is comprised between a maximum deformation of the oscillator and 50% of said maximum deformation.

FIGS. 3A to 3J schematically show the main technological steps of production of the oscillator 20 described with reference to FIGS. 2A to 2D. Each figure shows a cross section, cut perpendicularly to the main XY-plane, of a substrate 2 allowing the first plate 21 and the second plate 22 to be formed.

FIG. 3A shows an SOI substrate including a main layer $2_p$ of single-crystal silicon, of 5 μm thickness, a buried layer $2_b$ of 1.5 μm thickness, usually referred to by as the "buried oxide", and a carrier layer $2_k$, usually referred to as the "bulk" layer.

Figure 3B:
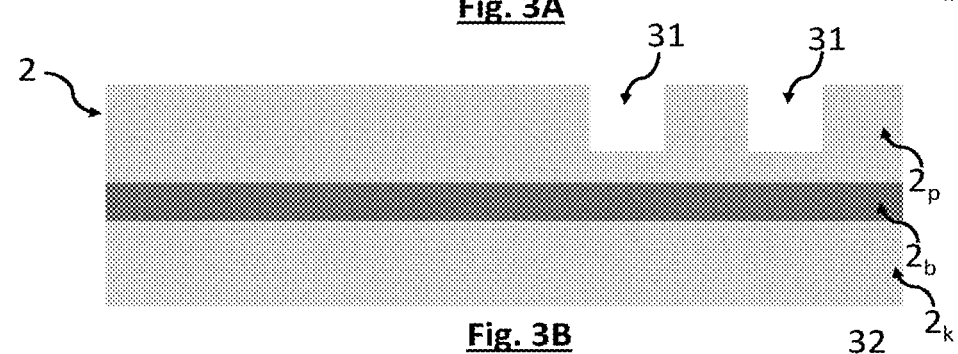

In a step shown in FIG. 3B, cavities 31, extending to a depth of 2 μm, are formed by photolithography followed by a dry etch.

Figure 3C:
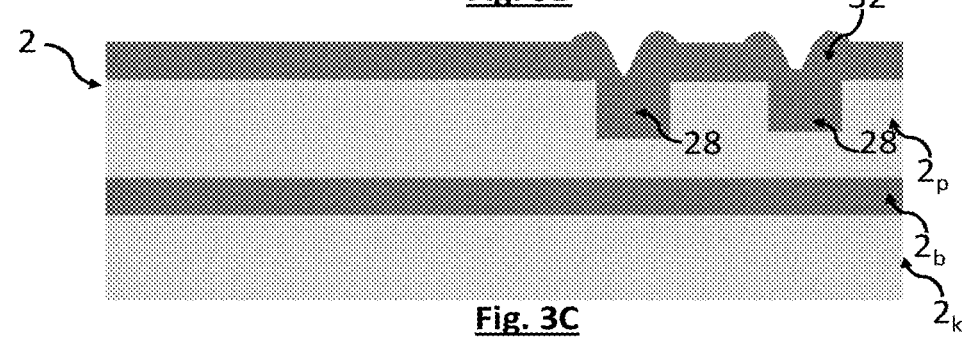

In a step shown in FIG. 3C, a layer 32 of silicon oxide ($SiO_2$) is deposited by plasma-enhanced chemical vapour deposition (PECVD). This allows the cavities 31 to be filled with silicon oxide, thereby allowing the solid channel 28 to be formed.

Figure 3D:
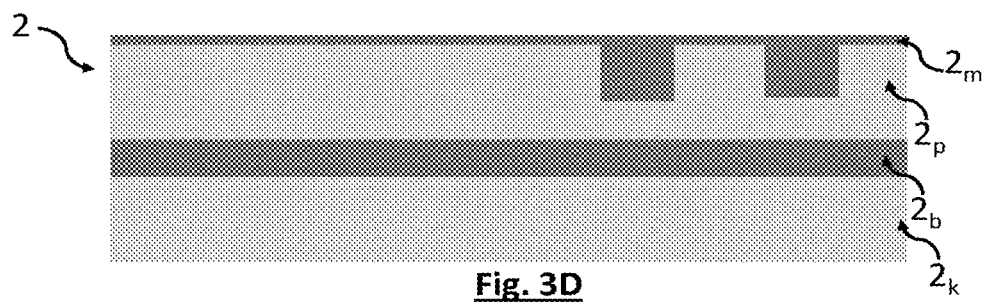

The oxide layer thus deposited is etched through a negative of the mask then chemical-mechanical polishing is carried out, so as to obtain a thin silicon-oxide layer, of thickness of about 100 to 200 nm, forming what is called an intermediate layer $2_m$, as shown in FIG. 3D.

Figure 3E:
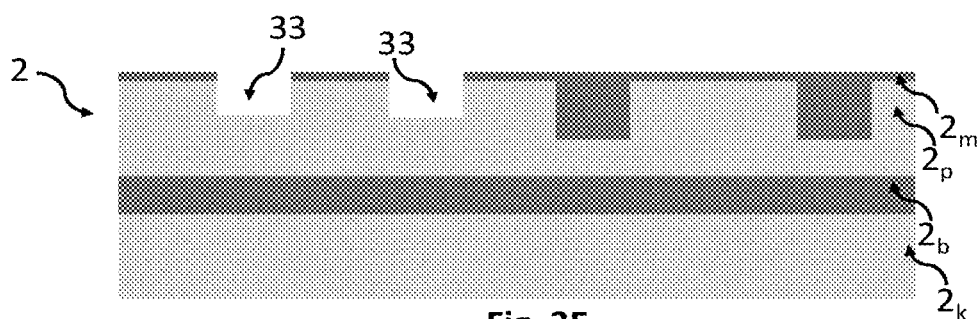

FIG. 3E shows the formation of fluidic cavities 33, of 4 μm depth, by photolithography and dry etching. The fluidic cavities form the fluidic channel 25.

Figure 3F:
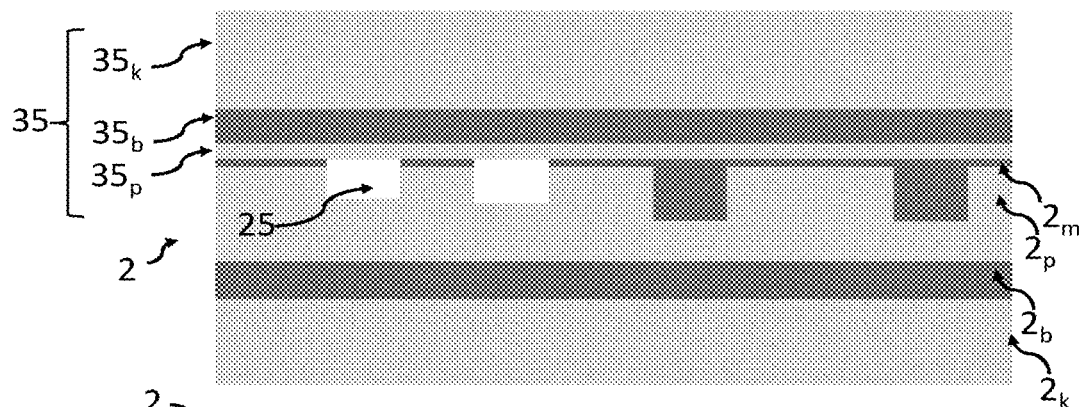
Figure 3G:
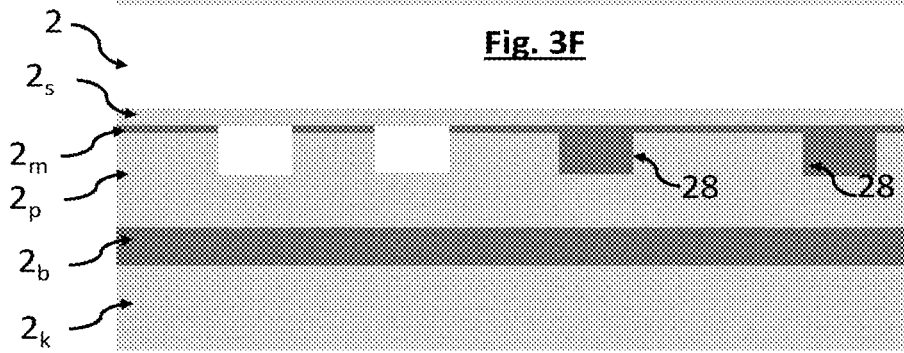

The substrate 20 is then covered by an auxiliary SOI substrate 35 including a main layer $35_p$ made of single-crystal silicon, a buried oxide layer $35_b$ and a lower layer $35_k$ of silicon, see FIG. 3F. The main layer $35_p$ of the auxiliary substrate 35 is deposited on the intermediate layer $2_m$ and bonded to the latter by molecular bonding. The buried oxide layer $35_b$ and the lower layer $35_k$ of the auxiliary substrate 35 are then removed by etching in order to leave only the optionally thinned main layer $35_p$ on the intermediate layer $2_m$, the main layer $35_p$ forming an upper layer $2_s$ of the substrate 2. This step is shown in FIG. 3G.

Figure 3H:
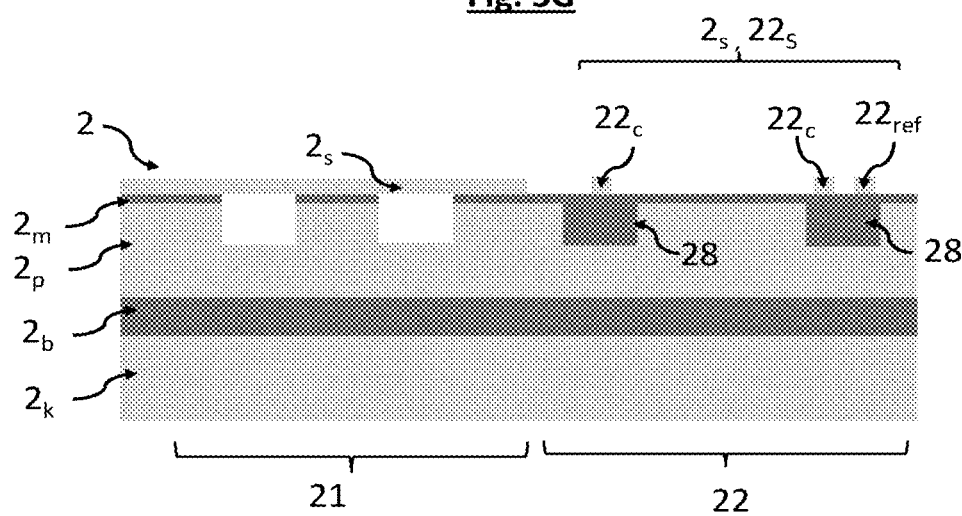

FIG. 3H shows a step of etching of the upper layer $2_s$, allowing the waveguide 26, and more precisely the upper layer $2_s$ of the plate 22, to be formed. In FIG. 3H, the portion of the substrate 2 corresponding to the first plate 21, and the portion of the substrate 2 corresponding to the second plate 22, have been shown. The layers $2_s$, $2_m$, $2_p$, $2_b$ and $2_k$ of the substrate form, in the first plate 21, the layers $21_s$, $21_m$, $21_p$, $21_b$ and $21_k$ and, in the second plate 22, the layers $22_s$, $22_m$, $22_p$, $22_b$ and $22_k$; see FIGS. 2B and 2C. The fluidic channel 25 is produced in the main layer $21_p$ and in the intermediate layer $21_m$ of the first plate. The solid channel 28 is produced in the main layer $22_p$ of the second plate, the core of the waveguide 26 being formed in the upper layer $22_s$ of the second plate. The intermediate layer $22_m$ has a small thickness, typically smaller than 200 nm, and has no influence on the waveguide.

Following the step shown in FIG. 3H, the gap 15 is etched in the substrate 2, as are the anchoring elements and the linking element 23. This allows the fixed portion 10 of the oscillator 20 to be defined.

Figure 3I:
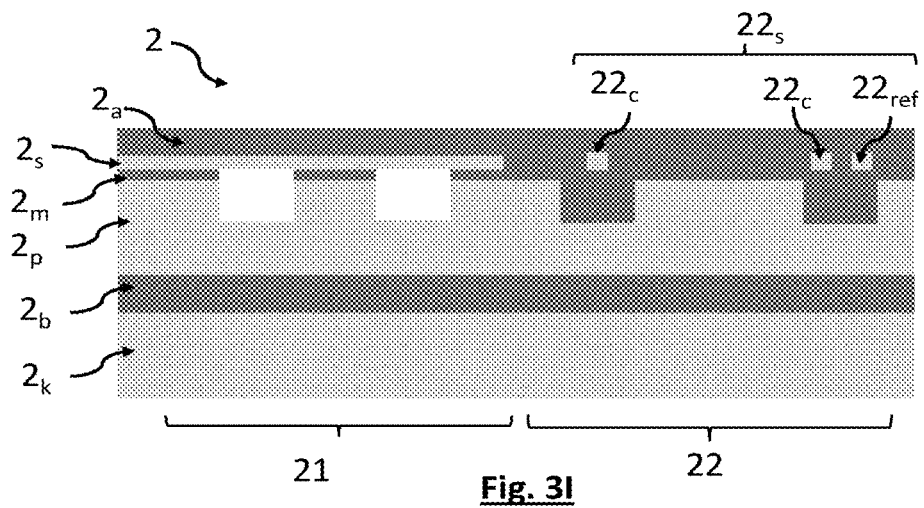

According to one variant, following the step shown in FIG. 3H, and prior to the etching of the gap, linking and anchoring elements, an encapsulating layer $2_a$ is deposited on the upper layer $2_s$, as shown in FIG. 3I. The encapsulating layer $2_a$ may be made of a third material, for example of silicon oxide, and be deposited by PECVD. Its thickness is for example comprised between 200 nm and 600 nm. The encapsulating layer $2_a$ allows the photonic circuit 26 produced in the plate 22 to be protected. It also defines a planar surface, on which other components may be formed, to be formed.

Figure 3J:
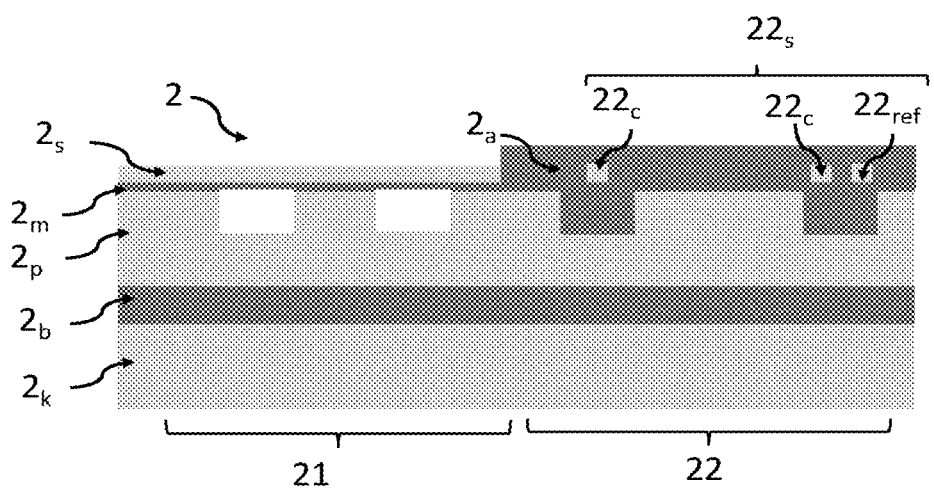

Optionally, the encapsulating layer may be removed from the portion of the substrate intended to form the first plate 21, as shown in FIG. 3J. According to this embodiment, the waveguide includes a third material that corresponds to the material of the encapsulating layer. In this example, the third material is identical to the second material forming the solid channel 28. As described above, the third material has a refractive index $n_3$ strictly lower than that of the first material, forming the upper layer $2_s$. In the second plate 22, the upper layer $2_s$ forms a layer $22_s$ corresponding to the core of the waveguide 26. The encapsulating layer $2_a$ and the solid channel 28 act in the waveguide as confining elements.

FIG. 4A schematically shows a variation in the resonant frequency f of the oscillator 20, formed by the first plate 21 and the second plate 22, during the detection of a particle 5 in the fluidic channel 25. The resonant peak is shifted by a variation δf in resonant frequency. An important element of the invention is the detection of the variation δf in resonant frequency with a photonic circuit integrated into the oscillator 20.

In a first configuration, which is schematically shown in FIGS. 2A and 2D or in FIG. 2E, the waveguide 26 forms an optical cavity $26_c$, which is able to confine the light, and a reference waveguide $26_{ref}$. The light source 6 injects a light wave 7 into the waveguide 26. Some of the light wave propagates to the detector through the reference waveguide $26_{ref}$ and forms a reference light wave $7_{ref}$. Some of the light wave is coupled to the resonant cavity $26_c$ and remains confined in the latter, thereby forming a confined light wave $7_c$. Some of the light wave $7_c$ guided in the resonant cavity $26_c$ undergoes decoupling, and is added to the reference light wave to form a resulting light wave 7', which is guided towards the photodetector 8 by the segment of light guide extending through the anchoring element $24_d$. Thus, the photodetector 8 detects the reference light wave $7_{ref}$ and some of the confined light wave $7_c$. The amount of light decoupled from the optical cavity depends on the geometry of the waveguide 26. It is for example small when the oscillator is at rest, the dimensions of the cavity then being optimized so that little light is decoupled to the photodetector. The deformation of the second plate 22 has the effect of modulating the optical decoupling of the cavity, thus modulating the intensity of the light wave detected by the photodetector. The deformation of the second plate 22 is symmetric with respect to the rest position of the oscillator. Two deformations, in opposite directions, take place during one oscillation period. The same goes for the waveguide 26, because the latter is integrated into the second plate 22. Thus, the intensity of the detected light wave is modulated at a modulation frequency w, such that w=2f. When the resonant frequency undergoes a variation δf, the modulation frequency w of the light amplitude detected by the photodetector 8 undergoes a variation of δw=2δf. Since the variation δf in frequency depends on the mass m of particles in the channel, according to a known function m=g(δf), the mass m may be obtained from a measurement of the variation δw in modulation frequency using the expression $$m = g\left(\frac{\delta w}{2}\right).$$

FIG. 4B schematically shows a variation Amax (t) as a function of time in the maximum amplitude Amax of the deformation of the plate as a function of time t, this amplitude being modulated at the resonant frequency f. FIG. 4C illustrates a variation S(t) as a function of time in the light signal S detected by the photodetector 8, the signal being minimal at each amplitude extremum and maximal when the amplitude is zero. The signal is modulated at the modulation frequency w.

In another configuration, shown in FIG. 2F, the variation in the resonant frequency of the second plate 22 is measured by optical interferometry, for example according to the principles of a Mach-Zehnder interferometer. In this configuration, the light wave emitted by the light source is divided between a light wave 7, which propagates through the waveguide 26 to the photodetector 8, and a reference light wave $7_{ref}$, which follows a reference optical path, and which also propagates to the photodetector 8. The reference light wave is guided by the reference photonic circuit $26_{ref}$ described with reference to FIG. 2F. The reference optical circuit defines a reference optical path. It is for example formed from mirrors or an optical fibre. The path of the reference light wave $7_{ref}$ is of set length and is, preferably, of similar length to the optical path traced by the light wave 7 when the plate 22 is at rest. Under the effect of the oscillation of the plate 22 at a resonant frequency f, the length of the optical path of the light wave 7 is modulated at a frequency 2f, whereas the length of the optical path of the reference light wave $7_{ref}$ remains the same. The reference light wave $7_{ref}$ and the light wave 7 propagating through the waveguide 26 are added upstream of the photodetector 8. Interference between the light wave 7 and the reference light wave $7_{ref}$ is detected by the photodetector 8, this interference producing a modulation of the signal S formed by the photodetector 8 at a modulation frequency w such that w=2f. When the resonant frequency undergoes a variation δf, the modulation frequency undergoes a variation δw=2δf. Since the frequency variation δf is dependent on the mass m of particles in the channel, according to a known function m=g(δf), the mass m may be obtained from the variation δw in modulation frequency, using the expression $$m = g\left(\frac{\delta w}{2}\right).$$

FIGS. 5A to 5F show various electrostatic actuation configurations of the oscillator 20. In each configuration, the actuation is achieved by means of at least:
one first electrode 11, which is securely fastened to the fixed portion 10 of the resonator, and subjected to a voltage including a first DC component $V_{DC}$ to which is added a first AC component $V_{AC}$;
one second electrode 12, which is securely fastened to the fixed portion 10 of the resonator, and subjected to a voltage including a second DC component, which in this example is the first DC component $V_{DC}$, to which is added a second AC component $V'_{AC}$, which is phase shifted by 180° with respect to the first AC component $V_{AC}$.

Figure 5A:
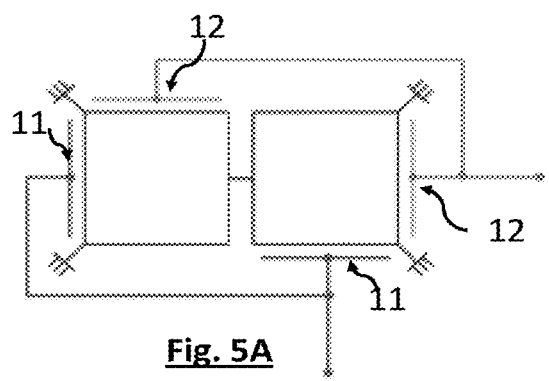
Figure 5B:
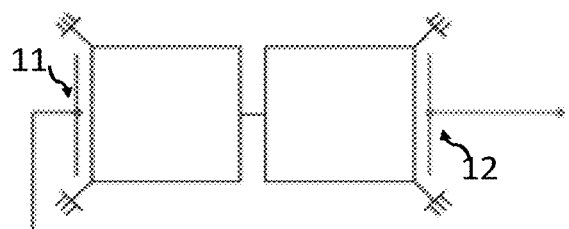
Figure 5C:
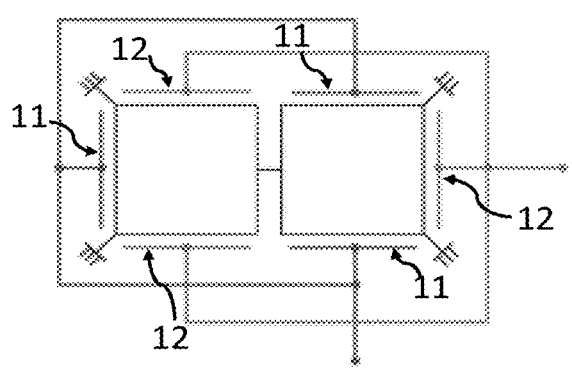
Figure 5D:
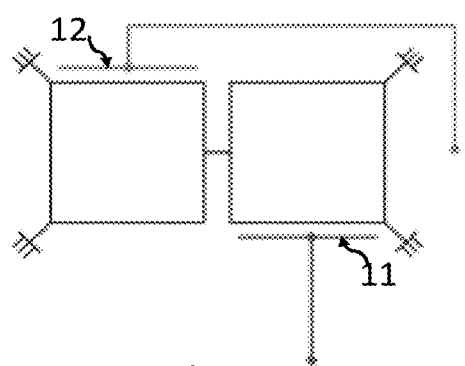
Figure 5E:
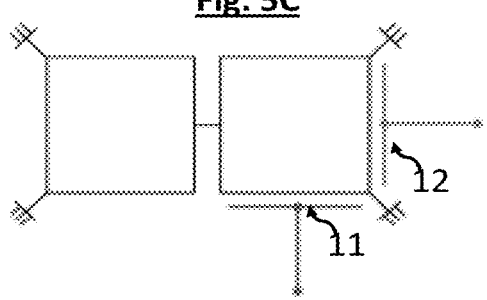
Figure 5F:
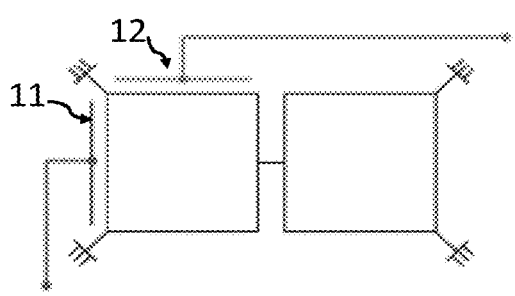

The configurations illustrated in FIGS. 5B, 5D, 5E and 5F correspond to minimal configurations, in which the oscillator is actuated by two electrodes that are out of phase with respect to each other, and preferably in phase opposition with respect to each other. The configuration shown in FIG. 5C is considered to be optimal, because the number of electrodes is maximized. This allows the strength of the electrostatic force applied to the oscillator 20 to be increased, the area of the oscillator facing the electrodes being increased.

The electrostatic force F(t), applied to the oscillator 20, at a time t, under the effect of the electrostatic actuation exerted by an electrode biased with an AC voltage V(t), may be expressed by the following relationship:

$$F(t) = \frac{\varepsilon_0 \varepsilon_r S}{2(g - \delta g)^2} V(t)^2, \quad (6)$$

where:
$\varepsilon_0$ and $\varepsilon_r$ are the dielectric permittivity of free space and of the ambient medium 3 in which the resonator is placed, respectively;
S is the area of the oscillator facing the electrode;
g is the thickness of the gap 15, separating the electrode from the oscillator;
$\delta g$ is the movement induced by the electrostatic force, i.e. a variation in g under the effect of said force. $\delta g$ is negligible with respect to g. In the given example, g=500 nm and $V_{AC}$=5 V. If a square plate of 100 μm side length and of 5 μm thickness is considered, $\delta g$ is about a few nm and therefore $\delta g \ll g$.

Generally, when the variation in mass is very small with respect to the actual mass $m_{\it eff}$ of the resonator, the mass resolution $\delta m$ of the resonator may be estimated using the following expression:

$$\delta m = 2 \frac{m_{\it eff}}{\omega_0} \delta \omega. \quad (7)$$

where $\omega_0$ is the resonant frequency of the resonator.

In the case of a square plate of 100 μm side length and of 5 μm thickness, if a gap of thickness g=500 nm, a voltage $V_{DC}$=100 V and a $V_{AC}$=2 V modulated with an angular frequency of w are considered, a mass resolution of the order of a few attograms is obtained.

FIGS. 6A, 6B and 6C show various configurations of anchoring elements 24 maintaining an oscillator 20 formed from two plates 21 and 22 joined by a linking element 23. FIG. 7A schematically shows a resonator including a first elementary oscillator 41 and a second elementary oscillator 42 that are disc-shaped and joined by a linking element 43, and four anchoring elements 24. FIG. 7B schematically shows a resonator including a first elementary oscillator 51 and a second elementary oscillator 52 that are ring-shaped and joined by a linking element 43, and four anchoring elements 24. FIG. 7C is a photograph of a resonator such as schematically shown in FIG. 7B.

In the various embodiments described above, the oscillator 20 includes two elementary oscillators that are connected by a linking element. The oscillator 20 may include a number of elementary oscillators higher than 2. In the embodiment described with reference to FIG. 8, the oscillator 20 includes a single oscillator 60 taking the form of a rectangular plate of length l and of width $$L = \frac{l}{2};$$

a first portion of which is passed through by a fluidic channel 65, similar to the fluidic channel 25 described above, and a second portion of which is passed through by a waveguide 66, similar to the waveguide 26 described above.

In FIG. 8, analogously to FIG. 1B, the oscillator has been shown immobile, in wireframe, and in movement.

The fluidic channel and the waveguide extend through a plurality of oscillation antinodes of the resonator 1. As described in the preceding examples, the deformation of the fluidic channel, at a resonant frequency, leads to a deformation of the waveguide, at the same resonant frequency. The resonant frequency may be detected by detecting a light wave travelling through the waveguide, by means of a photodetector coupled to the waveguide. The light wave resulting from the waveguide and reaching the photodetector is modulated at a frequency of modulation two times higher than the resonant frequency.

Oscillators according to the invention may be produced using fabrication processes that are known in the field of microelectronics, for example using fabrication substrates, i.e. what are usually called wafers, of 200 mm diameter in SOI technology.

The invention allows oscillators of large area, including various channels, through which various types of particles may flow, and in particular channels dedicated to particles of small size, and channels dedicated to particles of large size, to be obtained.

The invention claimed is:

1. An electromechanical resonator, comprising a fixed portion and an oscillator, the oscillator being configured to oscillate at a resonant frequency, the oscillator comprising:
    a fluidic channel, defining a fluidic circuit, produced in the oscillator, and configured to receive a fluid, the fluidic channel being further configured to oscillate at the resonant frequency, under the effect of the oscillation of the oscillator;

the electromechanical resonator further including:
    a waveguide, defining a photonic circuit, produced in the oscillator, and intended to guide a light wave between an input and an output of the waveguide, the waveguide being configured to oscillate at the resonant frequency, under the effect of the oscillation of the oscillator;
    the input of the waveguide being configured to be optically coupled to a light source, the output of the waveguide being configured to be optically coupled to a photodetector, so that the photodetector is configured to form a signal representative of the light wave propagated by the waveguide towards the photodetector, the light wave being modulated at a modulation frequency dependent on the resonant frequency;

such that when the mass of the fluid varies, inducing a variation in the resonant frequency, the variation in mass may be detected by measuring the modulation frequency or by measuring a variation in the modulation frequency of the signal formed by the photodetector.

2. The electromechanical resonator according to claim 1, wherein the fluidic channel and the waveguide extend, in the oscillator, while being, at least partially, symmetric with respect to each other.

3. The electromechanical resonator according to claim 1, wherein when the oscillator is configured to oscillate at an amplitude, the oscillator then comprising:
    oscillation antinodes, level with which the amplitude of the oscillation is maximal;

and oscillation nodes, level with which the amplitude of the oscillation is minimal;
the fluidic channel and the waveguide extending through at least one oscillation antinode.

4. The electromechanical resonator according to claim 1, wherein the waveguide comprises:
   a thin layer of a first material, of a first refractive index;
   a solid channel, formed from a second material, of a second refractive index, the second refractive index being strictly lower than the first refractive index, the solid channel being produced, in the oscillator, under the thin layer, such that the light wave is able to propagate, in the thin layer, facing the solid channel;
   a third material, of a third refractive index, the third refractive index being strictly lower than the first refractive index, the thin layer of first material lying between the solid channel and the third material.

5. The electromechanical resonator according to claim 4, wherein:
   the third material is formed by an ambient medium in which the electromechanical resonator is located;
   or the third material is formed by an encapsulating layer deposited on the thin layer of first material.

6. The electromechanical resonator according to claim 4, wherein the fluidic channel defines a fluidic volume, and wherein the solid channel defines a confining volume, the electromechanical resonator being such that the fluidic volume, multiplied by the density of the fluid intended to flow through the fluidic channel, is equal, to within 30%, to the confining volume multiplied by the density of the second material.

7. The electromechanical resonator according to claim 1, comprising at least one anchoring element, joining the oscillator to the fixed portion, the fluidic circuit and/or the waveguide extending along the anchoring element.

8. The electromechanical resonator according to claim 1, wherein the oscillator extends, in a main plane, along a width or a length or a diameter, the thickness of the oscillator, perpendicular to the main plane, being at least ten times smaller than the width, length or diameter.

9. The electromechanical resonator according to claim 1, wherein the oscillator comprises a plurality of elementary oscillators, such that:
   the fluidic circuit is produced in a first elementary oscillator; and
   the waveguide is produced in a second elementary oscillator, different from the first elementary oscillator;
   the first elementary oscillator and the second elementary oscillator being joined to each other by a linking element.

10. The electromechanical resonator according to claim 9, wherein the first elementary oscillator and the second elementary oscillator each extend, in a main plane, along a width or a length or a diameter, the thickness of each elementary oscillator, perpendicular to the main plane, being at least ten times smaller than the width, length or diameter.

11. The electromechanical resonator according to claim 1, comprising an actuating transducer, configured to induce an oscillation of the oscillator, the actuating transducer being:
   an electrode, configured to act on the oscillator by electrostatic transduction;
   or a piezoelectric element, joined to the oscillator.

12. The electromechanical resonator according to claim 1, wherein the waveguide comprises a reference waveguide that is optically coupled to a resonant optical cavity, such that the photodetector is configured to detect a light wave comprising:
   a reference light wave, which propagates through the reference waveguide;
   and a portion of a confined light wave, which propagates through the resonant optical cavity.

13. The electromechanical resonator according to claim 1, wherein the waveguide defines a guided optical path in the oscillator, and wherein the electromechanical resonator comprises a reference waveguide, extending out of the oscillator, and defining a reference optical path, the reference waveguide being configured to be coupled to the light source and to the photodetector.

14. A method for analysing a fluid, containing particles, using an electromechanical resonator according to claim 1, the method comprising:
   a) introducing the fluid into the fluidic channel;
   b) actuating the oscillator, so as to induce oscillations of the oscillator at a resonant frequency;
   c) illuminating the waveguide with a light source, which emits a light wave, such that the waveguide is able to propagate the light wave emitted by the light source through the oscillator;
   d) detecting, with a photodetector, a light wave transmitted by the waveguide, and modulated by the oscillation of the oscillator, and forming a signal representative of the detected light wave, the signal thus formed being modulated at a modulation frequency, the modulation frequency depending on the resonant frequency of the oscillator;
   e) estimating a mass of the fluid depending on the modulation frequency, or on a variation in the modulation frequency, of the signal formed in d).

15. The method according to claim 14, wherein d) comprises forming a signal of an interference between the light wave transmitted by the waveguide and a reference light wave emitted by the light source and transmitted by a reference waveguide.

16. The method according to claim 15, wherein the reference waveguide extends out of the oscillator.

17. The method according to claim 14, wherein the waveguide is able to confine the light wave emitted by the light source, a portion of the light wave, decoupled from the waveguide, propagating towards the photodetector, the intensity of the light wave decoupled from the waveguide being modulated at a modulation frequency dependent on the function of the resonant frequency of the oscillator.

* * * * *